(12) United States Patent
Chaggares et al.

(10) Patent No.: US 10,451,476 B2
(45) Date of Patent: Oct. 22, 2019

(54) MEMBRANE HYDROPHONE FOR HIGH FREQUENCY ULTRASOUND AND METHOD OF MANUFACTURE

(71) Applicant: FUJIFILM SonoSite, Inc., Bothell, WA (US)

(72) Inventors: Nicholas Christopher Chaggares, Whitby (CA); Oleg Ivanytskyy, Toronto (CA); Guofeng Pang, Ajax (CA); Marius Moszczynski, Toronto (CA)

(73) Assignee: FUJIFILM SONOSITE, INC., Bothell, WA (US)

( * ) Notice: Subject to any disclaimer, the term of this patent is extended or adjusted under 35 U.S.C. 154(b) by 492 days.

(21) Appl. No.: 15/241,021

(22) Filed: Aug. 18, 2016

(65) Prior Publication Data

US 2017/0052061 A1    Feb. 23, 2017

Related U.S. Application Data

(60) Provisional application No. 62/206,808, filed on Aug. 18, 2015, provisional application No. 62/297,763, filed on Feb. 19, 2016.

(51) Int. Cl.
*B06B 1/00* (2006.01)
*G01H 11/00* (2006.01)
(Continued)

(52) U.S. Cl.
CPC ............ *G01H 11/08* (2013.01); *B06B 1/0688* (2013.01); *B06B 1/0696* (2013.01); *G01H 3/005* (2013.01); *A61B 8/58* (2013.01)

(58) Field of Classification Search
USPC ........................................................ 367/149
See application file for complete search history.

(56) References Cited

U.S. PATENT DOCUMENTS 4,433,400 A * 2/1984 DeReggi ............... B06B 1/0688
310/800
4,517,665 A   5/1985 Dereggi et al.
(Continued)

FOREIGN PATENT DOCUMENTS

CN    2 919 209 Y    7/2007
EP    0 418 663 A1   3/1991
(Continued)

OTHER PUBLICATIONS

International Searching Authority, International Search Report and Written Opinion, PCT Patent Application PCT/US2016/047650, dated Nov. 25, 2016, 13 pages.
(Continued)

*Primary Examiner* — James R Hulka
(74) *Attorney, Agent, or Firm* — Baker Botts L.L.P.

(57) ABSTRACT

A membrane hydrophone for analyzing high frequency ultrasound transducers has a piezoelectric membrane with electrode patterns created on the surface of the membrane. In one embodiment, the electrode patterns are doubled on each side of the membrane except for an active area of the hydrophone. In one embodiment, the electrodes are formed by removing a conductive coating on the membrane with laser pulses. The laser is set to remove the conductive coating from the piezoelectric membrane from the same side of the membrane in order to accurately align the electrodes in the active area. In one embodiment, the active area of the hydrophone has an area in a range of 900-10,000 square microns.

17 Claims, 8 Drawing Sheets

(51) Int. Cl.
*G01H 11/08* (2006.01)
*G01H 3/00* (2006.01)
*B06B 1/06* (2006.01)
*A61B 8/00* (2006.01)

(56) References Cited

U.S. PATENT DOCUMENTS

| | | | | |
|---|---|---|---|---|
| 4,653,036 | A * | 3/1987 | Harris | B06B 1/0688 |
| | | | | 310/800 |
| 5,339,290 | A | 8/1994 | Greenstein | |
| 5,381,386 | A * | 1/1995 | Lum | B06B 1/0688 |
| | | | | 310/337 |
| 5,403,701 | A | 4/1995 | Lum et al. | |
| 5,479,377 | A | 12/1995 | Lum et al. | |
| 6,355,498 | B1 * | 3/2002 | Chan | B81C 1/00142 |
| | | | | 438/48 |
| 6,675,450 | B1 * | 1/2004 | Fetter | G01R 31/2824 |
| | | | | 216/13 |
| 7,296,329 | B1 * | 11/2007 | Barber | H03H 3/02 |
| | | | | 216/13 |
| 7,948,148 | B2 * | 5/2011 | Porat | A61K 9/0009 |
| | | | | 310/322 |
| 8,631,547 | B2 * | 1/2014 | Barber | H03H 3/02 |
| | | | | 29/25.35 |
| 2008/0028585 | A1 * | 2/2008 | Barber | H03H 3/02 |
| | | | | 29/25.35 |
| 2010/0094105 | A1 * | 4/2010 | Porat | A61K 9/0009 |
| | | | | 600/309 |

FOREIGN PATENT DOCUMENTS

| | | |
|---|---|---|
| JP | 04-032726 | 2/1992 |
| WO | 2017031375 A1 | 2/2017 |

OTHER PUBLICATIONS

Lum, P. et al. "A 150-MHz-Bandwidth Membrane Hydrophone for Acoustic Field Characterization," Hewlett-Packard Company, The Hewlett-Packard Journal, Aug. 1998, Article 1, pp. 6-18.
Supplementary European Search Report dated Apr. 24, 2019 in Application No. EP 16837875.

* cited by examiner

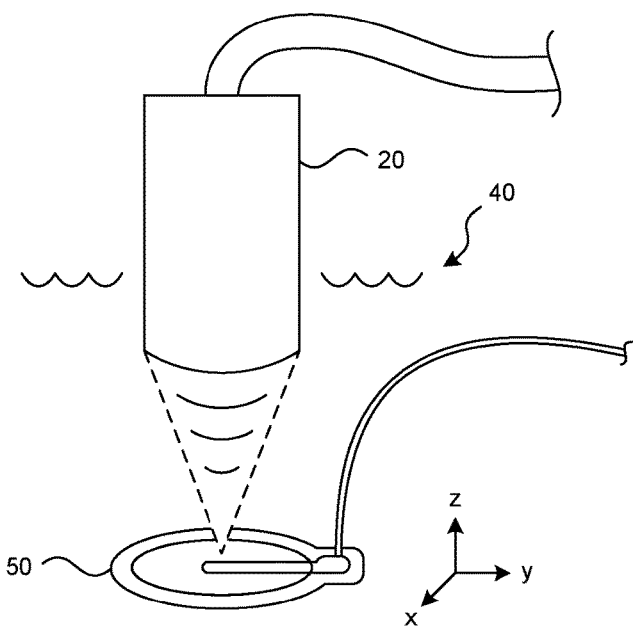
FIG. 2
*(Prior Art)*
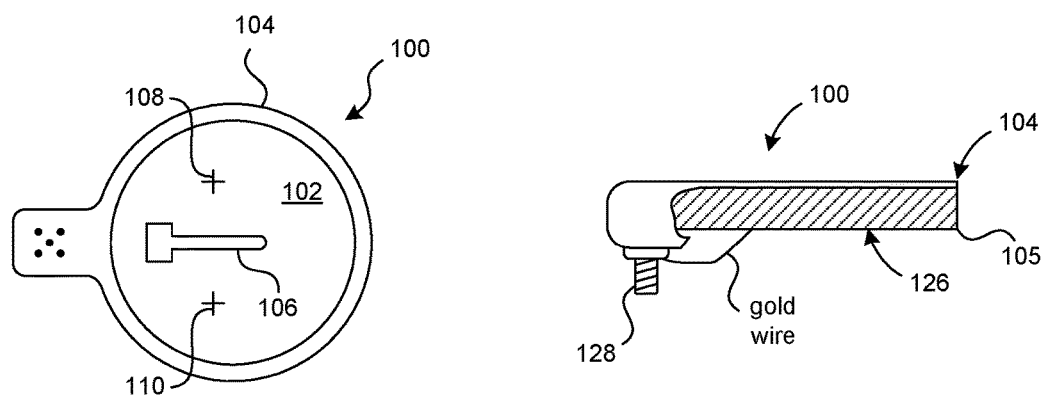
FIG. 3A                    FIG. 3B

MEMBRANE HYDROPHONE FOR HIGH FREQUENCY ULTRASOUND AND METHOD OF MANUFACTURE

RELATED APPLICATIONS

This application claims the benefit of U.S. Provisional Application Nos. 62/297,763 filed Feb. 19, 2016 and 62/206,808 filed Aug. 18, 2015, which are herein incorporated by reference in their entireties.

TECHNICAL FIELD

The disclosed technology relates to hydrophones for testing ultrasound transducers, and in particular to hydrophones used to test high frequency ultrasound transducers.

BACKGROUND

Ultrasound imaging operates by sending a number of short pulses of acoustic energy from a transducer into a region of interest and collecting the information contained in the corresponding echo signals. FIG. 1A shows a simplified ultrasound transducer having a number of individual transducer elements 12 (not drawn to scale) that vibrate and produce ultrasonic acoustic signals when a varying voltage is supplied across the elements. The elements also produce electronic signals when the elements receive acoustic energy. The elements 12 are typically arranged in a one or two-dimensional array that includes one or more matching layers 14 and a fixed lens 16. By carefully selecting the amplitude and the time at which the driving signals are applied to each of the transducer elements, the acoustic signals constructively combine to form a beam with a focal zone at a desired location. As the operating frequency of the transducer increases, the size of the focal zone (often the shape of a grain of rice) decreases. For example, at a 15 MHz center frequency, the size of the focal zone is about 500×300 μm. At 30 MHz, the size of the focal zone drops to approximately 280×150 μm. and at 50 MHz, the size of the focal zone is less than 200×100 μm. In addition to ultrasound arrays, ultrasound signals can also be generated by single-element transducers 17 as shown in FIG. 1B.

Ultra-high frequency (UHF) diagnostic ultrasound has progressed substantially in the past 10 years in both pre-clinical and clinical industries, with the introduction of systems with 50 MHz center frequency arrays having upper corner frequencies of over 70 MHz. There are many new scientific and medical possibilities that can be explored resulting from the higher resolution and bandwidth of UHF ultrasound, However, along with new applications and capabilities comes new testing and characterization challenges. As one skilled in the art will appreciate, as transducers push ever higher in frequency, wavelengths decrease accordingly, and various other mechanisms such as non-linear propagation of acoustic waves in water become more and more prevalent. There is currently a need to understand the character of UHF ultrasound in water both scientifically and for the purposes of regulation of medical and preclinical devices. In addition, to take advantage of modern sophisticated FEA modelling, there is a need to accurately measure acoustic fields at or even below the pitch of the array. There is clearly a need for smaller aperture hydrophones with higher frequency calibrations to ensure accurate measurement of harmonics and to reduce spatial uncertainties arising from short wavelength sound waves being measured with relatively large aperture hydrophones.

Before an ultrasound transducer can be approved for clinical use in the United States by the Food and Drug Administration (FDA) or can obtain the CE mark for clinical use in Europe, the acoustic energy produced by the transducer must be characterized. The characterization produces a map of the pressure intensities to make sure the focal zone is well defined and that the transducer is not producing hot spots of energy in undesired locations. Similarly, the characterization confirms that the energy produced is not so great that it will cause cavitation in tissue to be examined, and that power output is within acceptable limits imposed by various organizations. Well established standards exist to prescribe the testing protocols and results required for regulatory approval. However, UHF ultrasound has increasingly pushed these tests to the limits and beyond due to the lack of suitably small hydrophone aperture sizes and sufficiently high frequency calibration data.

As shown in FIG. 2, most transducer testing is performed by operating a transducer 20 in a liquid bath 40 (typically de-gassed water but could be another liquid). A hydrophone 50 is placed on a computer controlled stage (not shown) in the path of the ultrasound beam. As the transducer is operated, the stage is moved to cause the hydrophone to measure the location of the focal zone and the intensity of the beam at a number of locations. Signals from the hydrophone are stored by a computer system to confirm that the transducer is operating as intended. A plot of the intensity measurements in space defines the characteristics of the ultrasound transducer beam.

Membrane style hydrophones are the most desirable to use in sampling an ultrasound beam because of their flat frequency response and simple interactions with the radiation pattern created by the device under test (DUT). In order to be able to effectively sample the beam, the active area of the hydrophone must be substantially smaller than the focal zone of the transducer under examination. In the past, it has been difficult to reliably manufacture a membrane style hydrophone with a sufficiently small active area that can be used to test high frequency ultrasound transducers. Therefore, users have been forced to use needle-type hydrophones, which exhibit undesirable resonances and interactions with the radiation pattern being measured. In addition, specially shaped needle hydrophones that are designed to minimize unwanted resonances such as so called "lipstick style" hydrophones are used. However, in practice it is difficult to accurately manufacture such shapes to a small enough scale for very high frequency ultrasonic characterization. The result is that needle-type hydrophones are not as accurate in characterizing high frequency beam patterns as membrane style hydrophones.

Given these problems, there is a need for an improved high frequency membrane style hydrophone as well as a method for manufacturing such hydrophones.

SUMMARY

To address these and other problems, the technology disclosed herein relates to a novel membrane style hydrophone design and a method of manufacturing membrane style hydrophones for use in characterizing high frequency ultrasound transducers. Such characterizations can be used to certify transducers for clinical use but can also be used in the development and test of ultrasound transducer designs. In one embodiment, a hydrophone includes a piezoelectric membrane that is stretched across a support structure and coated on both sides with a conductive material such as a thin layer of gold or gold+chromium. A portion of the conductive material is then removed from each side of the piezoelectric membrane to create a positive electrode on one side of the membrane and a negative electrode on the other side of the membrane. The positive and negative electrodes overlap in a small area that defines an active area of the hydrophone. In one embodiment, the active area has a dimension that is between 10-30 microns in diameter.

In some embodiments, a patterning tool such as an excimer laser is used to selectively remove portions of the conductive material from the piezoelectric membrane to create the electrodes on the membrane. In one embodiment, conductive material on both sides of the membrane is removed by exposing the membrane to laser energy from the same side of the membrane e.g. without having to turn the piezoelectric membrane over. In some embodiments, one or more alignment features or fiducials are created in the membrane to allow the piezoelectric membrane to be accurately placed with respect to the coordinate system of the patterning tool. Once aligned, conductive material can be accurately removed from the membrane.

In some embodiments, the hydrophone includes overlapping positive and negative electrodes on both sides of the piezoelectric membrane with the positive electrode on one side of the membrane being electrically connected to the corresponding positive electrode on the other side of the membrane. Similarly, the negative electrode on one side of the membrane is electrically connected to the corresponding negative electrode on the other side of the membrane. In some embodiments, the overlapping electrodes are electrically connected with one or more conductive vias that are created in the piezoelectric membrane with the laser and filled with a conductive material.

An active area of the hydrophone is formed where a portion of the positive electrode on one side of the membrane overlaps with the negative electrode on the other side of the membrane.

In some embodiments of the disclosed invention, the device is fabricated from fully poled piezoelectric polymer or copolymer membrane to allow for maximum sensitivity achieved by aggressive polling of the raw film. This can lead to challenges related to spurious signals being detected in locations apart from the intended active aperture. In some embodiments of the disclosed technology, the piezoelectric membrane is fabricated into the device in an un-poled state, so that the electrodes may be used to spot pole the active area. This approach can reduce or eliminate many spurious signals but may result in decreased sensitivity and spot size variations. In some embodiments, overlaying like-polarity electrodes are used to clamp electric fields in the membrane achieving greater spatial specificity in spot polling thus yielding more precise and predictable active spot size.

In some other embodiments, portions of the piezoelectric membrane are selectively de-poled prior to coating it with the conductive material in order to reduce the electrical response of the membrane to received acoustic energy in undesirable locations, thus allowing for more aggressive polling of the entire membrane (as compared to spot poling). In one embodiment, the piezoelectric membrane is selectively de-poled in areas away from the active area of the hydrophone. In one embodiment, the laser patterning tool is used to de-pole the piezoelectric membrane, by modifying the polymer with UV laser energy such that the membrane remains mechanically intact but is less piezoelectrically efficient, in all areas of the hydrophone except for the active area. In still another embodiment, un-poled piezoelectric copolymer membrane is fabricated into the device, a laser patterning tool is used to modify the membrane reducing the piezo electric potential of the membrane in all areas except the active area, ensuring that spot polling can only occur effectively in the unmodified active area, electrodes are deposited such that they are aligned to the active area and the membrane is spot polled. In yet another embodiment, the previous approach is combined with overlaying like-polarity electrodes design to achieve an extremely well defined active aperture after spot polling.

BRIEF DESCRIPTION OF THE DRAWINGS

FIG. 2 illustrates a conventional system for testing ultrasound transducers with a hydrophone;

FIGS. 3A and 3B illustrate an exemplary high frequency membrane hydrophone in accordance with an embodiment of the disclosed technology;

DETAILED DESCRIPTION

Figure 1B:
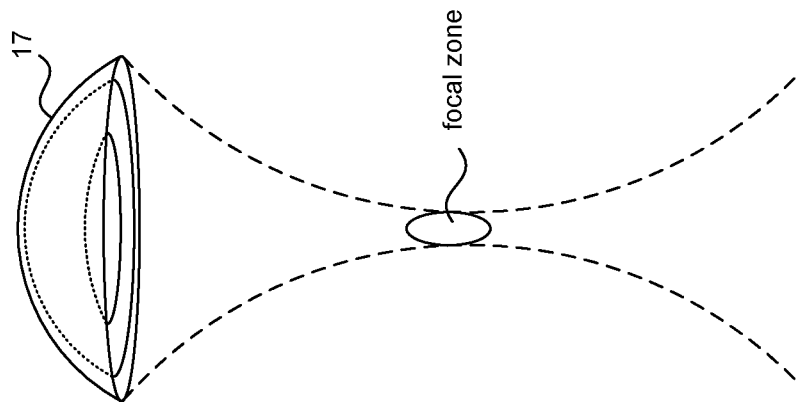
FIG. 1B illustrates a beam pattern formed by a conventional single-element ultrasound transducer.
Figure 1A:
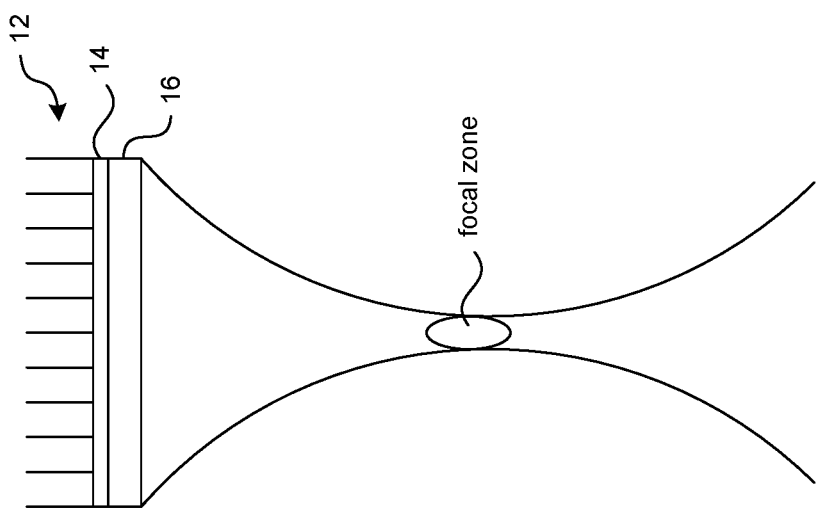
FIG. 1A schematically illustrates a beam pattern formed by a conventional ultrasound transducer array

As will be described in further detail below, the disclosed technology is a membrane style hydrophone with one or more small active areas that can be used to characterize high frequency ultrasound transducers. In one embodiment, a membrane is made of a thin film piezoelectric co-polymer such as P(VDF-TrFE) having a thickness that is, for example, between 3-12 microns thick. However, other thicknesses or other piezo materials (such as PVDF) could be used. The membrane is preferably stretched across a frame in a manner that removes any wrinkles from the membrane. In one embodiment, the membrane is held on an outer hoop and then simultaneously stretched about its perimeter by an inner hoop that circumferentially presses a portion of the membrane into a groove to stretch it free of wrinkles like a drum head. Once the membrane is stretched, the membrane is adhered to a circular frame that fits within the inner hoop and the excess membrane outside of the frame is cut off. The frame is then used to form a portion of the hydrophone. In one embodiment, the frame has a diameter of approximately 2 cm. but larger or smaller frames could be used.

The frame is mounted to a metal support and then coated with a metallic conductor such as gold or gold+chromium (or other metallic conductor) by a sputtering or another process. In one embodiment, the thicknesses of the conductor placed on the membrane is 1500-2500 angstroms thick. However much thinner or thicker conductor coatings could be used, such as, but not limited to 300 angstroms to 5000 Angstroms.

The conductive coating on both sides the membrane is then patterned to form an overlapping portion of conductors on the top and bottom surfaces of the membrane that forms the active area of the hydrophone. The overlapping conductive areas must be precisely aligned and in some embodiments are on the order of 10-30 microns across, which before the techniques described in U.S. Provisional Application No. 62/206,808 was not possible to reliably manufacture.

FIGS. 3A and 3B show one embodiment of a hydrophone 100 constructed in accordance with an embodiment of the disclosed technology. The hydrophone 100 includes a generally round disc of a piezoelectric membrane 102 that is glued to a circular frame 104, which in turn is secured to a support 105. In one embodiment, the support 105 is a made of a conductive metal such as titanium. A first electrode 106 is patterned on one side of the piezoelectric membrane while a second electrode (not shown) is patterned on the other side of the piezoelectric membrane. In some embodiments, the piezoelectric membrane may include a pair of registration features or fiducials 108, 110 (not drawn to scale) that are cut through the piezoelectric membrane in order to allow the membrane to be aligned with a laser patterning system. The registrations features can be created with a laser and can have virtually any shape (square, rectangles, crosses etc.) In one embodiment the registration features are squares of approximately 10 microns per side. The corners of the registration features allow the piezoelectric membrane to be aligned with a sub-micron level of accuracy.

With both sides of the membrane coated with a metallic conductor, an excimer laser or other patterning tool is used to remove portions of the conductive coating from the surfaces of the piezoelectric membrane in such a manner that the membrane is relatively unaffected.

In one embodiment, once an electrode pattern is created on the first side of the membrane, the membrane is turned over and aligned to the patterning tool using the one or more registration features 108, 110. Once aligned, the patterning tool forms the electrodes on the second side of the membrane. In one embodiment of the disclosed technology, an electrode on the first side of the membrane forms a positive electrode of the hydrophone while a second, larger electrode on the other surface of the piezoelectric membrane is grounded.

In another embodiment that is described in detail below, a substantial majority of the electrodes on both sides of the membrane can be created by exposing a single side of the membrane to laser energy. In this embodiment, the registration features or fiducials may not be needed.

A thin wire 120 (e.g. a gold bonding wire, or a sliver plated copper buss wire) can be connected to a first electrode on the membrane. In addition, bonding wires can be connected to a second electrode as well or if the frame 104 and/or support 105 is conductive, the frame can be used to connect to the second electrode. In one embodiment, an acoustically matching elastomer 126 is poured over the back side of the hydrophone. In another embodiment, the matching elastomer may be omitted leaving a both sides of the membrane with the respective electrodes uncovered for maximum sensitivity. In one embodiment, the elastomer 126 is made of a silicone rubber having an acoustic impedance that closely matches that of water.

In some embodiments, it may be advantageous to mount a buffer amplifier to a printed circuit board that is placed on the support 105 or to mount the buffer amplifier directly onto the membrane of the hydrophone. The buffer amplifier can increase the gain of the signal produced and/or buffer the signal so that it can be carried by a signal cable (not shown). In one embodiment, the support 105 of the hydrophone is fitted with an SMA or other style connector 128. The SMA connector 128 is a coaxial connector where the outer shield is connected to the conductive support 105 or to the negative electrode and a center conductor is connected to the positive electrode (or the output of the buffer amplifier if used). The connections to the SMA connector could also be reversed if desired.

Figure 4:
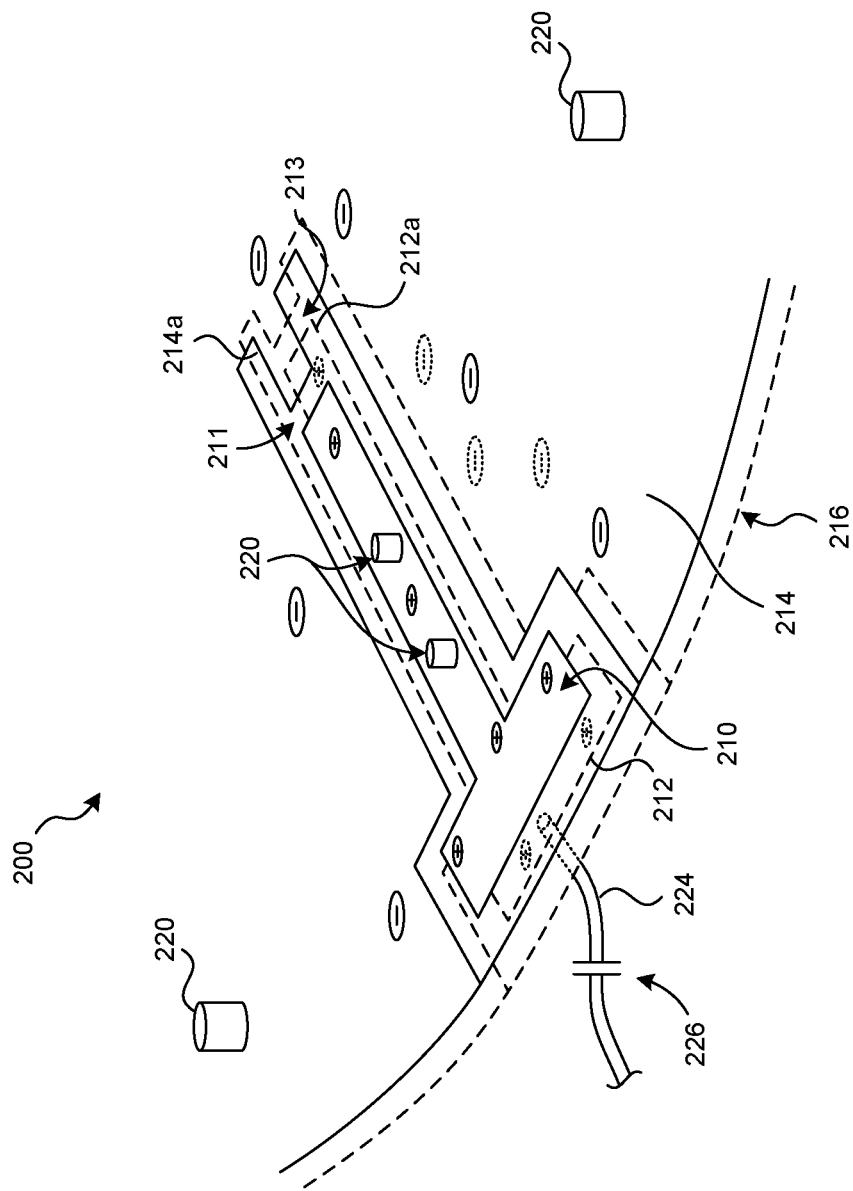
FIG. 4 illustrates a partial three-dimensional cut away view of a membrane style hydrophone constructed in accordance with one embodiment of the disclosed technology.

Another embodiment of a membrane hydrophone is shown in FIG. 4. In this embodiment, the conductor on the membrane is patterned to create substantially matching electrodes on the top surface and on the bottom surface of the membrane. In this embodiment, the two positive electrodes on the top and bottom surfaces of the piezoelectric membrane overlap each other and the two negative electrodes on the top and bottom surfaces of the piezoelectric membrane overlap each other. The positive electrode on the top surface does not overlap the negative electrode on the bottom surface (or vice versa) except in the active area of the hydrophone. FIG. 4 is a partial, three-dimensional, cross-sectional view of a hydrophone 200 with the electrode patterns shown in solid lines being on the top surface of the membrane and the electrode patterns shown in dashed lines being on the bottom surface of the membrane. The top surface of the membrane includes a T-shaped electrode 210 (not drawn to scale) that is surrounded by a ground plane or ground electrode 214. A substantially identical T-shaped electrode 212 is formed on the bottom surface of the membrane and is located directly beneath the electrode 210 on the top surface of the membrane. A corresponding ground plane or ground electrode 216 having substantially the same shape as the ground plane electrode 214 is located on the bottom surface of the membrane directly below the ground plane 214 that is on the top surface of the membrane. In some embodiments, the ground plane electrodes 214, 216 are separated from the positive electrodes 210, 212 by a gap that surrounds the perimeter of the positive electrodes on all sides.

In some embodiments, the positive electrodes on the top and bottom surface of the piezoelectric membrane and the negative or ground plane electrodes on the top and bottom surface of the piezoelectric membrane are electrically connected. In some embodiments, one or more vias 220 are filled with a conductive epoxy or other conductive material to electrically connect the top positive electrode 210 to the bottom positive electrode 212. Similar one or more filled vias electrically connect the top ground plane electrode 214 with the bottom ground plane electrode 216. The vias can be formed with a laser to burn a hole though the piezoelectric membrane, which is then filled with a conductive material such as a conductive epoxy. The vias 220 could also remain unfilled, and be sputtered through, if they were cut into the membrane before the membrane was sputtered. If the frame or a portion thereof that supports the stretched piezoelectric membrane is conductive, then the electrodes 214, 216 can be electrically connected through the frame and vias for the larger negative electrodes 214, 216 could be eliminated. In the embodiment shown, the overlapping T-shaped electrodes 210, 212 are the positive electrodes for the hydrophone while the overlapping ground planes 214, 216 are electrically grounded. However, the polarities could be reversed.

In the membrane hydrophone, there is a tab portion 212a of the bottom positive electrode 212 that underlies a correspondingly shaped tab portion 214a of the top ground plane electrode 214. The overlap between the two tab portions 212a, 214a forms the active area of the hydrophone, which produces a signal when exposed to acoustic energy. In some embodiments, the area of the overlapping positive and ground electrodes is about 900 square microns. However, the overlapping area (or active area) of other embodiments of the hydrophone disclosed herein could be between about 100 square microns and about 10,000 square microns. However, larger or smaller overlapping regions could also be used. The optimum size of the active area is dependent on the operating frequency of the ultrasound transducer to be analyzed. If the active area is too small, sensitivity may be too low resulting in unacceptable SNR, increased uncertainty, and increased testing time. On the other hand, if the active area is too large, then spatial averaging may cause inaccuracies that lead to unacceptable spatial and spectral uncertainties.

In the embodiment shown, there is a gap 211 between the tab portion 214a of the ground plane 214 and the positive electrode 210 on the top surface of the membrane. Similarly, there is a gap 213 between the tab portion 212a of the positive electrode 12 and the surrounding ground plane 216 on the bottom surface of the membrane. In one embodiment, the gaps 211, 213 are straight so that the overlapping portion of the electrodes (e.g. the active area) is generally square. In another embodiment, the gaps could be curved so that the active area is generally circular. Other shapes of the active area (ovals, star shapes etc.) can also be created with the patterning tool.

In one embodiment, the gaps, 211 and 213 have a similar width of about 5 um. However, they could be as small as about 1.5 μm up to as much as 100s of microns. The gap 211 could be the same width as the gap 213 or they could be different widths. The width of the gaps combined with the length of the active area defined by the overlying area of tabs 212a and 214a can be tailored in conjunction with gaps 211 and 213 to control the effective spot size of the active area by taking into account non-normal electric field components within the membrane. For example, if a square effective active area is desired, a smaller overlapping length may be employed by decreasing the distance between the proximal edges of gaps 211 and 213 with respect to the width of the tabs 212a and 214a.

An electrical conductor 224 connects the signal electrodes 210, 212 to a broad band buffer amplifier (not shown) that amplifies the signals produced by the overlapping regions of the electrodes when exposed to high frequency ultrasound signals. In the embodiment shown, the conductor 224 is connected to the positive electrode 212 on the underside of the hydrophone. However, the conductor could be connected to the positive electrode on the top surface of the hydrophone. In one embodiment, the signal electrode is capacitively coupled to the broad band buffer amplifier to ensure no DC offset exists between the signal and ground electrodes. In one embodiment, the signal electrode may be connected to an input of the broad band amplifier by a series connected capacitor 226 of about 10 nF in value. One skilled in the art will understand that other values could be used depending on the frequency and impedance characteristics desired. In one embodiment, the ground planes 214, 216 are shorted to the frame that supports the membrane with solder.

Figure 5A:
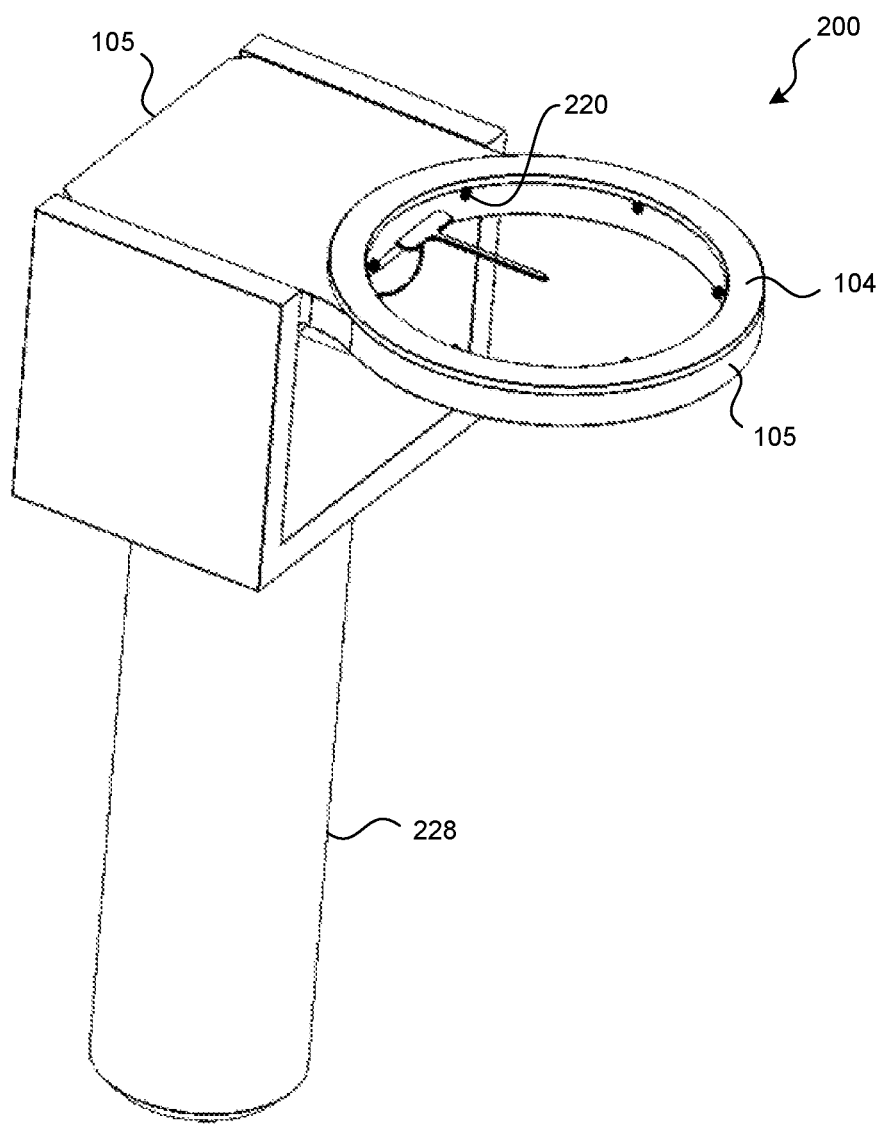
FIGS. 5A illustrates a complete hydrophone mounted on a supporting post in accordance with one embodiment of the disclosed technology.

Signals from the amplifier can be carried by a co-axial cable, or other electrical conductor, to receiving electronics (not shown) that store and analyze the signals to characterize the beam pattern produced by an ultrasound transducer. As shown in FIG. 5A, the completed membrane hydrophone is secured to a post 228 that allows the hydrophone to be mounted in a movable stage that is positioned at various locations with respect to the transducer being tested. FIG. 5A is drawn more to scale and in the embodiment shown, the length of the T-shaped electrode is approximately 7.5 mm, while the length of the overlapping electrode sections is approximately 30 μm. For comparison, a grain of beach sand is 100 μm or larger. Therefore, a precise patterning tool is required to accurately form the overlapping areas on the membrane.

To create the electrode patterns, the conductive coating on the membrane is patterned with a laser that removes the conductor but does not harm the membrane itself. In one embodiment, a first laser pulse removes the conductor on the top surface of the membrane and a second pulse at the same location (and on the same side of the membrane) removes the conductor on the bottom surface of the membrane. To create the T-shaped electrodes, doubles pulses are therefore used to outline the shape of the T-shaped electrodes 210, 212. To form the gap 211 between the end of the T-shaped electrode 210 and the tab portion 214a of the ground plane 214, the size of the laser pulse is set to the desired size of the gap and single pulses are used to remove only the conductor on the top surface of the membrane as the laser is moved. Precise control of the laser pulse ensures the removal of electrode material on only one side of the membrane, leaving the electrode on the other side undamaged.

To form the gap 213 between the tab portion 212a of the bottom T-shaped electrode 212 and the surrounding ground plane 216, the membrane is flipped over and single pulses are used to remove the conductor on the bottom surface of the membrane. Because the membrane is substantially transparent to both visible and UV light when the conductor is removed, registration of the membrane with the alignment system of the laser is simplified. In addition, because majority of the top and bottom electrodes can be patterned from same side of the membrane using the laser, the alignment of the top and bottom electrodes is highly accurate. Accurate electrode definition and small precise gaps 211 and 213 allow for a highly accurate and predictable active area, which is critical as the active area dimensions become closer to the thickness of the membrane, allowing for precise control and minimization of non-normal electric field components.

Although the disclosed embodiment uses T-shaped electrodes, it will be appreciated that other shapes such as "I-shaped" or "L-shaped" electrodes or other shapes could be used.

The use of the double electrodes on both sides of the piezoelectric membrane has proven to be advantageous, particularly when using pre-poled membranes in construction of the hydrophone. In the embodiment shown, the overlapping electrodes force zero (or near zero) electric field conditions in all areas of the membrane containing the signal electrode traces and all areas containing the ground electrodes. In some previous embodiments, it was found that due to the slight conductivity of water and the sensitive electronics in a buffer circuit that connects to the electrode and the thin piezoelectric membrane, a hydrophone without the double electrodes did not require a ground electrode to produce a signal and that any unclamped signal traces may generate spurious signals. This condition is particularly exacerbated by the use of thin piezoelectric membranes that are desirable in the high frequency hydrophones described as very small amounts of charge are detected in the sensitive electronics required to measure signals from the active area.

In another embodiment, it is possible to begin with an un-poled film. The electrodes are created and the active area spot-poled using a suitable combination of voltage and temperature applied to the active area. Using an unpoled film in conjunction with the double electrode design, followed by spot polling virtually eliminates signals outside of the very accurately defined active overlapping area defined by tabs 214a and 212a and gaps 211 and 213.

In the embodiment shown, a rectangular or square active area in the electrode design was employed in order to simplify the laser fabrication of the hydrophone for development. The disclosed techniques could be adapted to produce a round electrode as described above. Any electrode shape that can be made through photo-ablation laser masks (e.g. round, square, oval, or even star-shaped) can be made with the removal of the metallic conductor through the piezo membrane (registration through membrane without cutting membrane.)

In some embodiments conductor removal is further enhanced by a weak metal etch (5% acetic acid for example) that is applied to the finished electrode pattern to ensure that no conductive metal remains in the areas that have been photo-ablated by the laser. While it is likely possible to remove 100% of the metal electrode with the laser, perfectly tuning the laser to achieve 100% electrode removal is challenging. Therefore, in one embodiment, the hydrophone membrane is immersed in a weak chemical etch designed to remove 100-200 Angstroms of metal ensuring that any remnants of the electrode that may have been left behind after photo-ablation are removed from the surface of the membrane. As will be understood by persons skilled in the art, this chemical etch process can be fine-tuned in many ways to optimize material removal as desired.

Additionally, in one embodiment, the electrodes on both sides of the membrane may be coated in a thin photo resist or other material capable of resisting the wet etch material, and the laser may be used to remove both the resist and conductor material to produce the required electrode pattern. As one skilled in the art will appreciate, when such a resist layer is used, the wet etch employed may be much more aggressive without risking deterioration of the desired remaining electrodes. Care must be taken to understand the laser interaction with the photo resist to properly account for the absorption of laser energy by the resist for this method to be employed in the special gap regions used to create the overlapping electrode areas 212a and 214a. However, resist may be easily employed in any area where both top and bottom electrodes are to be removed with multiple laser pulses. Wet etch must be carefully selected, however, to ensure chemical and thermal compatibility with the thin polymer membranes used for construction of the small aperture hydrophones described herein.

The technology disclosed herein allows removing nearly perfectly registered areas of electrode material from both the front and back sides of the hydrophone by controlling the properties of the laser used to remove the electrode material such that the conductor on the front and rear sides of the membrane may be removed from the same side of the membrane. This allows nearly the entire electrode pattern to be created from one side of the membrane ensuring submicron accuracy of the front side of the hydrophone with respect to the back side of the hydrophone.

In some embodiments, the disclosed technology also includes vias to connect the overlapping electrodes from front to back electrically. The vias can be created with a laser or other means and a conductive epoxy or other conductive means (sputtering, wires, etc.) used to conductively connect the front and the rear electrode. Although means other than vias (e.g. wires) might be employed to electrically connect the electrode on one side to the corresponding electrode on the other side, vias allow for very low impedance and low inductance connections to be made simply using lasers to cut though the membrane with little or no mechanical stress. Such low inductance and low impedance connections ensure that the membrane can be clamped to a near zero electric field between the electrodes even in highly dynamic RF conditions.

Figure 6:
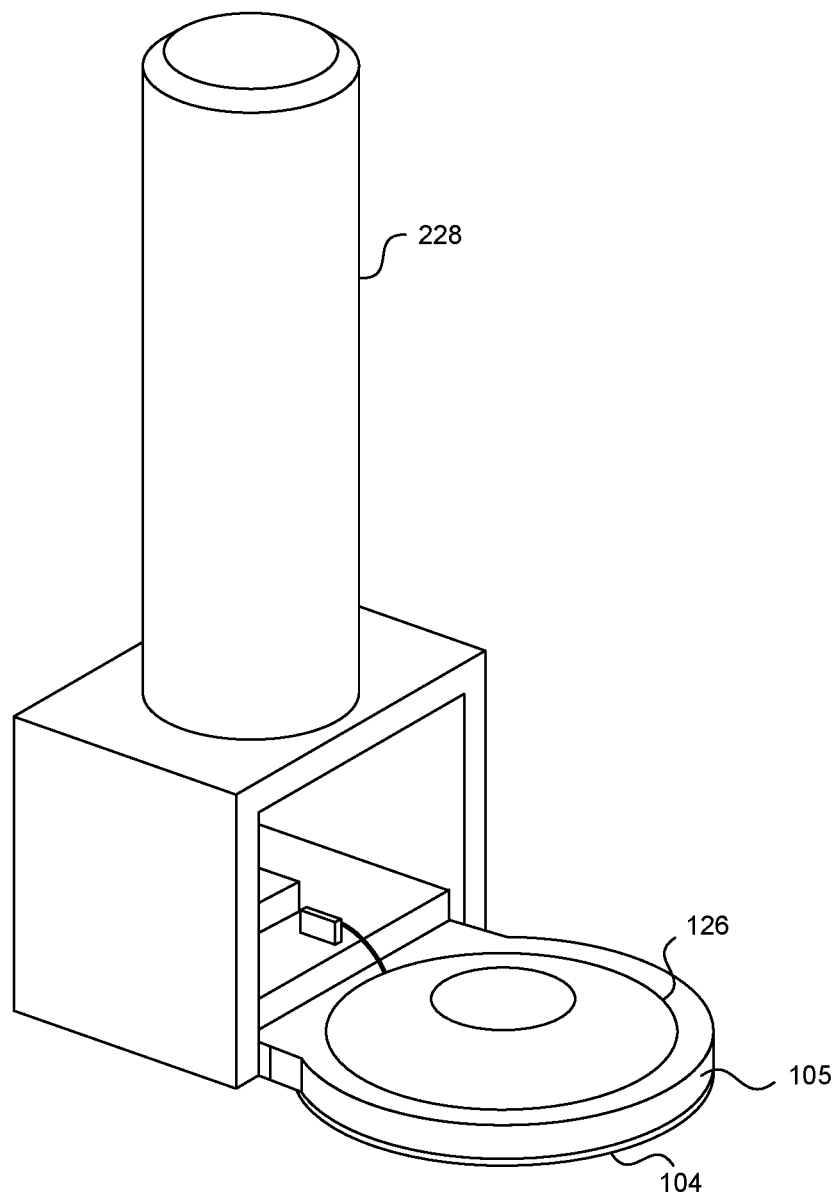
FIGS. 6 illustrates a bottom surface of a hydrophone coated with an elastomer acoustically well matched to water in accordance with an embodiment of the disclosed technology.

After the electrode patterns and vias are completed, one embodiment covers the rear or bottom electrodes with a polymeric elastomer 126 such as silicone covering the rear signal and ground electrodes as shown in FIG. 6. As one skilled in the art will understand, some silicones have a very good acoustic match to water and a relatively high acoustic loss at high frequency with very high electrical insulating characteristics that prevent the signal electrode from creating any spurious acoustic signals in the region of the single electrode isolation band. The silicone also serves to protect the electrode and membrane from wear and tear and greatly enhances the stiffness of the membrane allowing for faster scanning and less rigorous vibration reduction specifications for the scanning system. Other polymers such as epoxy or engineering plastics well matched to water such as TPX or LDPE or elastomers such as polyurethane or latex materials or specially developed acoustic polymer materials could be used as an acoustic backing or covering as long as they are well matched to water and can be applied to the thin hydrophone membrane with low stress (e.g. poured on in liquid form and cured in place).

Figure 5B:
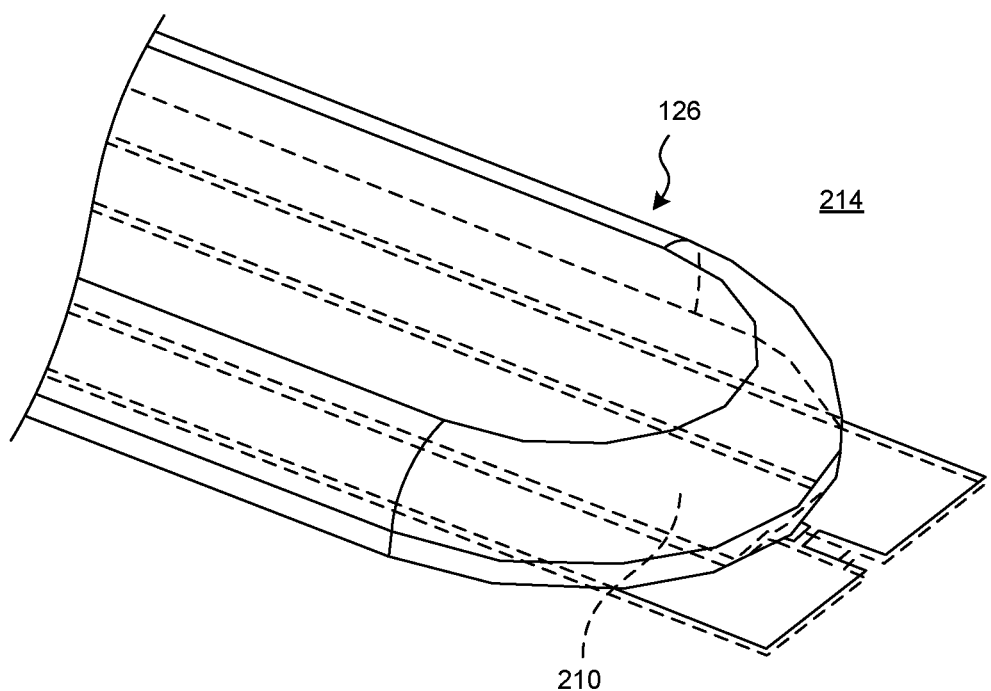
FIG. 5B illustrates a portion of an electrode on a top surface of a hydrophone that is coated with an elastomer material acoustically well matched to water in accordance with an embodiment of the disclosed technology.

As shown in FIG. 5B, in some embodiments a portion of the positive electrode on the top surface of the membrane is also covered by the acoustic matching elastomer 126. In one embodiment, the elastomer is applied over the top electrode using a toothpick or other small applicator under a microscope. However, it will be appreciated that other precision material deposition tools could be used. In the embodiment shown, there is no acoustic matching elastomer over the active area of the hydrophone.

In one embodiment, the electrodes are patterned on the coated P(VDF TrFE) membrane using a UV laser that is tuned to remove the electrode material in 1 pulse from the front of the membrane and from the rear of the membrane in a second pulse, leaving the membrane itself undamaged. A single area of the front electrode is removed from the membrane to isolate the signal electrode from the ground plane/electrode on the front side of the membrane. The membrane is then flipped over and visually aligned to the pattern on the rear of the membrane (that was created by laser ablation through the transparent membrane). Once aligned, a single area of the rear electrode is removed to isolate the signal electrode from the ground plane/electrode on the rear side of the membrane. A portion of the ground electrode pattern on the front side of the membrane overlaps a portion of the signal electrode pattern on the rear side of the membrane (or vice versa). This is the only place on the membrane where the signal and ground electrodes overlap. There are only two places on the membrane where electrode exists and is not overlapping (e.g. the small isolation regions or gaps 211 and 213 defining the overlapping electrodes).

In one embodiment, the conductive material is Cr/Au applied at a thickness of 1900 angstroms (other conductive materials and thickness could be used). The conductive material is removed from both the front and rear faces of the membrane by ablation with an excimer laser acting through a mask and 10× reduction optics from one side of the membrane. The laser wavelength is set to 248 nm and the fluence selected to be below the ablation threshold of the membrane. In one embodiment, the fluence is selected to be 0.25 J/cm2. This pulse characteristic allows for the electrode material to be removed in a single pulse from the front surface of the membrane without affecting the electrode on the rear surface. A second identical pulse is then used to remove the conductive material from the rear surface of the membrane. This is done without adversely affecting the membrane itself. This approach removes the challenge of aligning the edges of the overlapping electrodes on opposite sides of the membrane.

Other combinations of laser power/wavelength/fluence can be used to remove the top electrode without affecting the bottom electrode or to remove both the top and bottom electrode. The goal is to use a laser pulse that is not significantly absorbed by the polymer membrane used for the piezo element, but is strongly absorbed by the electrode material. In one embodiment, a 248 nm excimer laser with pulses of ~15 ns duration was used. Additionally, the use of photo-ablation allows for complex patterns to be focused on the membrane, thereby allowing the gaps to be made in a single pulse.

In accordance with one embodiment of the disclosed technology, a high frequency membrane hydrophone includes a piezoelectric membrane that has a conductive material on opposite sides thereof. If it is desired to create the electrodes by ablating the conductor from each side of the membrane, then it is advantageous to form one or more registration features on the front and rear electrode material by ablation on the front surface and through-membrane ablation of the rear surface, ensuring excellent registration of front and rear side fiducials. A first side of the piezoelectric membrane includes a first electrode pattern that is formed by removing some of the conductive material. A second side of the piezoelectric membrane includes a second electrode pattern that is formed by removing some of the conductive material. The first and second electrode patterns overlap in an active area of the hydrophone.

Figure 7:
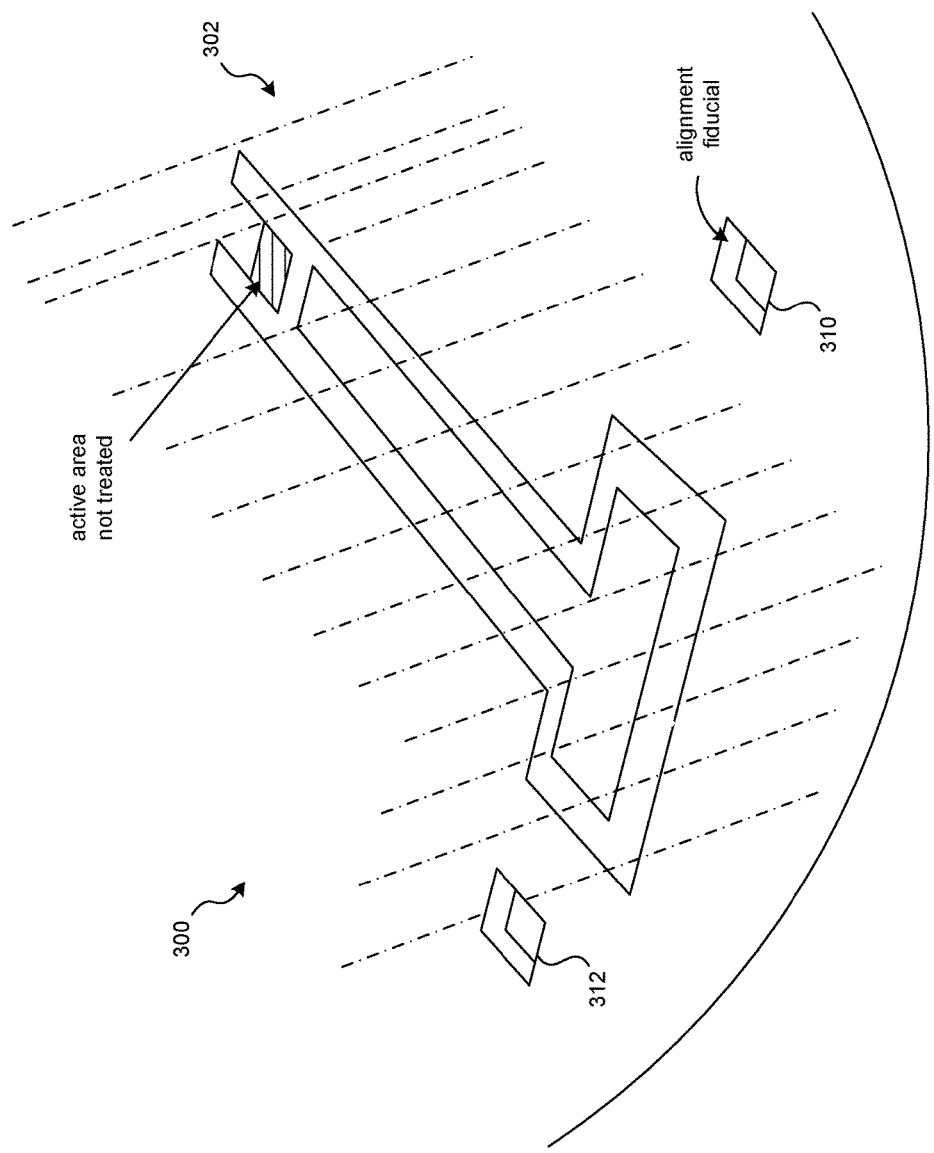
FIG. 7 illustrates how a piezoelectric membrane can be treated prior to the application of a conductor in accordance with another embodiment of the disclosed technology.

In some embodiments, it is advantageous to "de-pole" the piezoelectric membrane in areas except for the active area of the hydrophone. FIG. 7 shows a portion of a piezoelectric membrane 300 that is treated by the laser over a region 302 in a manner that reduces the piezoelectric response of the membrane. In one embodiment, the treatment occurs in all areas except for the active area of the hydrophone. The treatments are performed prior to applying the conductive coating over the membrane. In one embodiment, one or more fiducials 310, 312 are created in the membrane so that the active area of the hydrophone can be formed on the area that was left untreated once the electrode patterns are formed.

The treatment performed by the laser modifies the piezoelectric membrane so that the membrane is less responsive to received acoustic energy. This reduces artifacts created by the areas of the electrodes other than those created by the active area. In one embodiment, the treatment in the area 302 is performed by patterning the piezoelectric membrane with a series of pulses at about 15 ns with a laser fluence of between 0.5 and 1 J/cm2 and a pulse repetition frequency of about 20 Hz.

Figure 8:
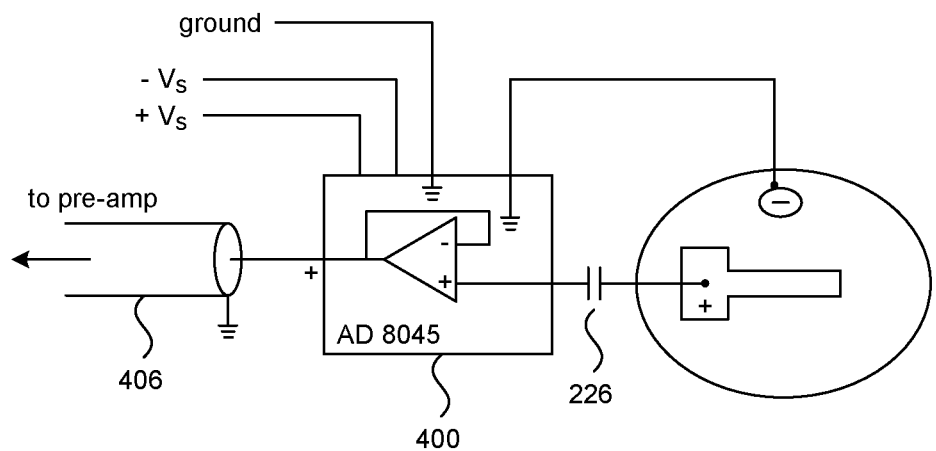
FIG. 8 illustrates one embodiment of a buffer circuit used to condition signals from the membrane style hydrophone in accordance with another aspect of the disclosed technology.

FIG. 8 illustrates a circuit for receiving and buffering the signals produced by the hydrophone prior to being transmitted to processing electronics in a remote computer system (not shown). The circuitry includes a buffer amplifier 400, which in one embodiment is an integrated circuit (model number AD8045 from Analog Devices) connected in a unity gain configuration having a positive input that is connected via a capacitor 226 to the positive electrode of the hydrophone. The negative electrode on the hydrophone is connected to a ground connection on the printed circuit board. A co-axial cable 406 is used to carry the signals amplified by the buffer amplifier 400 to further signal processing circuitry (pre-amp, A/D converters, DSPs etc.) Positive and negative voltage supplies for the buffer amplifier as well as a ground connection for a printed circuit board on which the buffer amplifier is mounted are supplied via separate wires. In one embodiment, the printed circuit board that is carried on the support 126 of the hydrophone. The entire circuit board is potted in a water-proof sealant so that the circuitry will operate under water.

Figure 9:
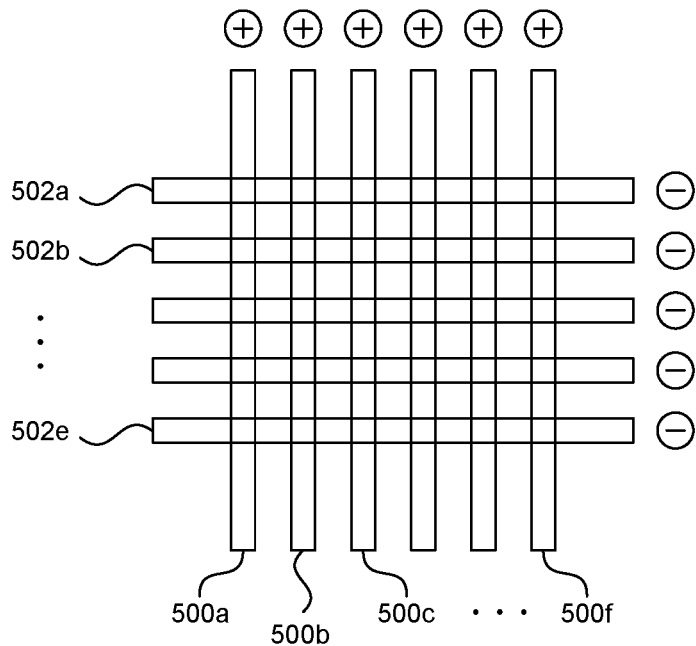
FIG. 9 illustrates an array style membrane hydrophone having a number of active areas constructed in accordance with another embodiment of the disclosed technology.

FIG. 9 shows an alternative embodiment of a hydrophone constructed in accordance with an embodiment of the disclosed technology. In this embodiment, a grid hydrophone includes a number of thin electrodes on each surface of the membrane. The individual electrodes overlap each other at a number of locations that form a number of active areas of the hydrophone. In the embodiment shown, a number positive electrodes 500a, 500b . . . 500f are patterned on one side of the membrane and a number of negative electrodes are formed on the other side of the membrane. An active area of the hydrophone is formed at each location where a positive electrode overlaps with a negative electrode. As will be appreciated, each of the electrodes must be individually connected to either separate buffer amplifiers or to a common buffer amplifier using a multiplexer or the like.

The array type hydrophone shown in FIG. 9 allows multiple locations to be sampled by selecting which positive and negative electrode are to be connected to the receive electronics and the hydrophone itself does not have to be moved. In one embodiment, the overlapping electrodes can be made by patterning each side of the membrane or areas requiring the removal of material from both sides can be patterned from a single side of the film as described above.

As higher frequency ultrasound finds additional clinical uses, high frequency ultrasound transducers will need to be tested to make sure they are safe for use on patients. The disclosed technology allows membrane hydrophones to be manufactured with small enough active areas such that they can be used to analyze beam patterns from these high frequency ultrasound transducers having center frequencies of 20-50 MHz and higher.

From the foregoing, it will be appreciated that specific embodiments of the invention have been described herein for purposes of illustration, but that various modifications may be made without deviating from the scope of the invention. Accordingly, the invention is not limited except as by the appended claims.

We claim:

1. A membrane hydrophone for measuring acoustic energy from a high frequency ultrasound transducer, comprising:
  a frame;
  a piezoelectric membrane having a first side and a second side that is supported by the frame and including a conductive material on both sides of the piezoelectric membrane; and a first electrode pattern comprising a first electrode and a second electrode pattern comprising a second electrode formed within the conductive material, wherein the first electrode pattern and second electrode pattern overlap each other on opposite sides of the piezoelectric membrane to define an active area of the hydrophone;

wherein the first electrode pattern comprising the first electrode is created on both the first and second sides of the piezoelectric membrane and overlap each other except in the active area, and wherein the second electrode pattern comprising the second electrode is created on both the first and second sides of the piezoelectric membrane and overlap each other except in the active area.

2. The membrane hydrophone of claim 1, wherein the first electrode patterns on each side of the piezoelectric membrane are electrically coupled together.

3. The membrane hydrophone of claim 2, further comprising one or more conductive vias in the piezoelectric membrane that electrically couple the first electrode patterns on each side of the piezoelectric membrane.

4. The membrane hydrophone of claim 1, further comprising a buffer amplifier to amplify the signal produced by the active area of the hydrophone, wherein an input to the buffer amplifier is capacitively coupled to the first or second electrode pattern on the membrane.

5. The membrane hydrophone of claim 1, further comprising at least one registration feature cut into the piezoelectric membrane with a laser.

6. The membrane hydrophone of claim 1, wherein the active area of the hydrophone has an area of less than 1600 square microns.

7. The membrane hydrophone of claim 1, wherein the active area of the hydrophone has an area of less than 900 square microns.

8. A method of making a membrane hydrophone for measuring acoustic energy from a high frequency ultrasound transducer, comprising:

stretching a piezoelectric membrane across a frame;

applying a conductive layer to a first side and a second side of the piezoelectric membrane; and selectively removing a portion of the conductive layer on the piezoelectric membrane to create a first electrode pattern comprising a first electrode and a second electrode pattern comprising a second electrode that overlap in an active area of the hydrophone, wherein the first electrode pattern and the second electrode pattern are created on both the first and the second side of the piezoelectric membrane;

wherein the conductive layer is removed by applying laser energy to the conductive layer to remove a portion of the conductive layer and leaving the piezoelectric membrane intact.

9. The method of claim 8, wherein the conductive layer is selectively removed by:

applying laser energy to the conductive layer on the first side of the piezoelectric membrane to create the first electrode pattern on the first side of the membrane; and applying laser energy to the first side of the piezoelectric membrane in a location where the conductive layer has been removed from the first side of the piezoelectric membrane to create the first electrode pattern on the second side of the piezoelectric membrane, wherein the first electrode pattern on the first and second sides of the piezoelectric membrane overlap each other except in the active area of the hydrophone.

10. The method of claim 8, wherein the conductive layer is applied with a sputtering tool.

11. The method of claim 8, wherein the electrodes are created by applying a chemical etch to the piezoelectric membrane after a portion of the conductive layer has been removed from the piezoelectric membrane with the laser.

12. The method of claim 8, wherein the electrodes are created by removing the conductive coating from the piezoelectric membrane with a combination of laser patterning of a resist layer and chemical etch.

13. The method of claim 8, further comprising creating conductive vias in the piezoelectric membrane to electrically connect the electrode patterns on each side of the piezoelectric membrane.

14. The method of claim 8, further comprising: treating areas of the piezoelectric membrane to reduce a piezoelectric characteristic of the membrane except for the active area of the hydrophone prior to the applying of the laser energy to the conductive layer.

15. The method of claim 8, further comprising spot polling the active area of the membrane by applying a voltage to the first and second electrode patterns on the piezoelectric membrane.

16. A membrane hydrophone for measuring acoustic energy from a high frequency ultrasound transducer, comprising:

a piezoelectric membrane having a first side and a second side;

a first electrode on the first side and the second side of the piezoelectric membrane;

a second electrode on the first side and the second side of the piezoelectric membrane, whereby the first and second electrodes overlap in an area between 10-30 microns in diameter; and at least one registration feature that is cut though the piezoelectric membrane that allows the piezoelectric membrane to be aligned with an electrode patterning tool.

17. A membrane hydrophone for measuring acoustic energy from a high
frequency ultrasound transducer, comprising:

a piezoelectric membrane having a first side and a second side;

a first plurality of electrodes on the first side of the piezoelectric membrane; and a second plurality of electrodes on the second side of the piezoelectric membrane, whereby the first plurality and the second plurality of electrodes on the surfaces overlap in a grid-pattern of active areas.

* * * * *